US006984486B1

(12) United States Patent
Schubert et al.

(10) Patent No.: US 6,984,486 B1
(45) Date of Patent: Jan. 10, 2006

(54) SYNTHETIC PEPTIDE OF REGULATORY VIRUS PROTEIN R (VPR) OF HUMAN IMMUNODEFICIENCY VIRUS TYPE 1 (HIV-1) AND THE UTILIZATION THEREOF

(75) Inventors: Ulrich Schubert, Bethesda, MD (US); Peter Henklein, Berlin (DE); Victor Wray, Wolfenbuttel (DE)

(73) Assignee: J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 09/913,927

(22) PCT Filed: Feb. 19, 2000

(86) PCT No.: PCT/DE00/00525

§ 371 (c)(1),
(2), (4) Date: Jan. 14, 2002

(87) PCT Pub. No.: WO00/49038

PCT Pub. Date: Aug. 24, 2000

(30) Foreign Application Priority Data

Feb. 19, 1999 (DE) ............................ 199 08 752
Feb. 19, 1999 (DE) ............................ 199 08 766

(51) Int. Cl.
*C12Q 1/70* (2006.01)
*C07K 7/00* (2006.01)
*C07K 14/16* (2006.01)
*C07K 17/00* (2006.01)
(52) U.S. Cl. .................. 435/5; 530/324; 530/325; 530/326; 530/327; 530/402; 530/810
(58) Field of Classification Search ............... 530/324, 530/325, 326, 327, 402, 810; 514/12–14; 424/188.1; 435/5, 235.1, 236
See application file for complete search history.

(56) References Cited

U.S. PATENT DOCUMENTS

| | | | |
|---|---|---|---|
| 5,580,739 A | 12/1996 | Alizon et al. | |
| 5,639,619 A | 6/1997 | Chen et al. | |
| 5,721,104 A | 2/1998 | Chen et al. | |
| 5,780,238 A | 7/1998 | Weiner et al. | |
| 6,001,985 A | 12/1999 | Kappes et al. | |
| 6,340,461 B1 * | 1/2002 | Terman ................... | 424/193.1 |

FOREIGN PATENT DOCUMENTS

| | | |
|---|---|---|
| WO | WO 94/19456 | 9/1994 |
| WO | 95/23631 * | 10/1995 |
| WO | WO 95/26361 | 10/1995 |
| WO | 96/08970 * | 3/1996 |
| WO | WO 96/07741 | 3/1996 |
| WO | WO 96/08970 | 3/1996 |
| WO | 98/08375 * | 3/1998 |
| WO | 98/32456 * | 7/1998 |
| WO | WO 98/44945 | 10/1998 |
| WO | WO 99/09412 | 2/1999 |

OTHER PUBLICATIONS de Rocquigny et al (Journal of Biological Chemistry 272: (49):30753-9, 1997).*
De Rocquigny et al (Journal of Biological Chemistry 272: 30753-30759, 1997).*
Cornille et al (J. Peptide Res. 53:427-435, 1999).*
H. Gras-Masse et al., 1990, "A synthetic protein . . . patients," Int. J. Peptide Res. 36:219-226.
F. Cornille et al., 1999, "Efficient solid-phase . . . studies," Database Accession No. XP002145861, J of Peptide Res. 54:427-435 (Abstract only).
M. Nishizawa et al., 1999, "A Carboxy-Terminally . . . Cycle," Virology, 263:313-322.
B.P. Roques et al., 1997, "Structure, biologically . . . NCp7," Biochimie, 79:673-680.
H. de Rocquigny et al., 1997,"The Zinc Fingers . . . Vpr*," The Journal of Biological Chemistry, 272(49):30753-30759.
L.D. Shostak et al., 1999, "Roles of p53 . . . vpr," Experimental Cell Research, 251:156-165.
W. Schuler et al., 1999, "NMR structure of the . . . functions," Database Accession No. XP002145860, N of Molecular Biolody, 285(5):2105-2117 (Abstract only).
K. Wecker et al., 1999, "NMR structure of the . . . Vpr," Database Accession No. XP002145862, Europ J of Biochem, 266(2):359-369 (Abstract only).
Z. Luo et al., 1998, "Structural studies of . . . Protein," Database Accession No. XP002145859, Biochem and Biophys Res Comm 244(3):732-736.
A. Adachi, 1986, "Production of acquired immunodeficiency . . . clone," J Virol 59:284-291.
C. Arunagiri et al., 1997, "A C-terminal domain of HIV-1 . . . lymphocytes," Apoptosis 2:69-76.

(Continued)

*Primary Examiner*—Mary E. Mosher
(74) *Attorney, Agent, or Firm*—Gates & Cooper LLP

(57) ABSTRACT

The invention pertains to synthetic (s) peptides derived from the viral regulatory protein R (Vpr) of the human immunodeficiency virus type 1 (HIV-1), particularly the chemical synthesis of the 96 amino acid full length Vpr protein ($sVpr^{1-96}$), of a 47 amino acid long N-terminal ($sVpr^{1-47}$), of a 49 amino acid long C-terminal fragment ($sVpr^{48-96}$) as well as fragments thereof ($sVpr^{1-20}$ and $sVpr^{21-40}$) and further approximately 15 amino acid long fragments of $sVpr^{1-96}$. As fragments or full length products of the HIV-1 regulatory protein, those products are used in biological assays, for molecular and structural characterization of Vpr and domains thereof, as well as for the development of anti-Vpr antibodies directed against Vpr peptide sequences.

12 Claims, 10 Drawing Sheets

OTHER PUBLICATIONS

Figure 1:
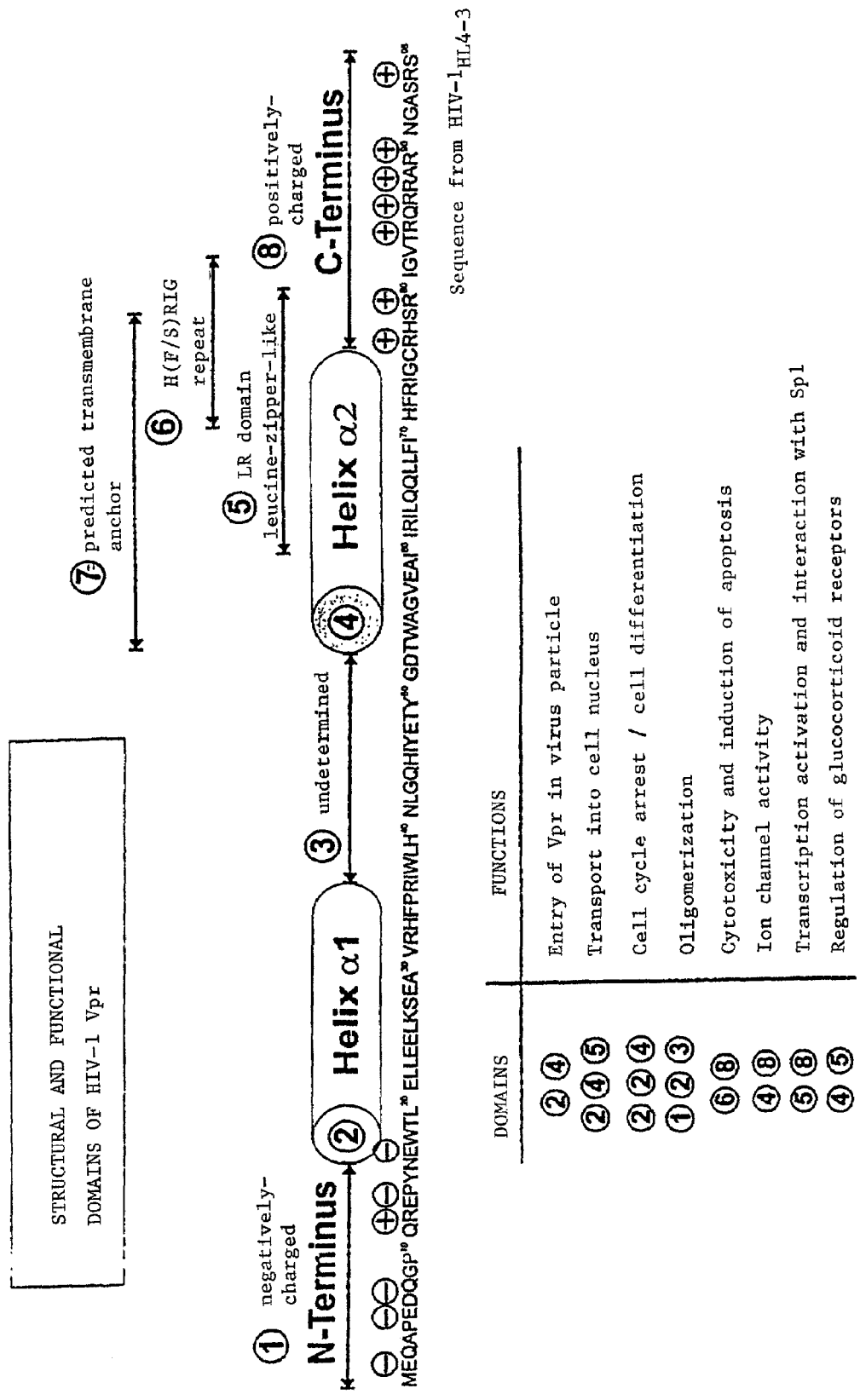

J.W. Collman et al., 1992, "An infectious molecular clone of an . . . type 1," J Virol 66:7517-7521.

D.N. Levy et al., 1994, "Serum Vpr Regulates Productive Infection and Latency of Human Immunodeficiency Virus Type 1," Proc Natl Acad Sci USA 91:10873-10877.

I.G. Macreadie et al., 1996, "Extracellular addition of a domain . . . death," Mol Microbiol 19:1185-1192.

I.G. Macreadie et al., 1997, "Cytocidal activities of . . . yeast," Protein and Peptide Letters 4:181-186.

S. Mahalingam et al., 1997, "Nuclear import, virion . . . Vpr," J Virol 71:6339-6347.

S.C. Piller et al., 1996, "Vpr protein of human . . . bilayers," Proc Natl Acad Sci USA, 93:111-115.

S. Yao et al., 1998, "Helical structure of polypeptides . . . Vpr," Protein and Peptide Letters 5:127-134.

L.J. Zhao et al., 1994, "Biochemical mechanism . . . protein," J Biol Chem 269:15577-15582.

L.J. Zhao et al., 1994, "Biochemical mechanism . . . domain," J Biol Chem 269:32131-32137.

\* cited by examiner

SYNTHETIC PEPTIDE OF REGULATORY VIRUS PROTEIN R (VPR) OF HUMAN IMMUNODEFICIENCY VIRUS TYPE 1 (HIV-1) AND THE UTILIZATION THEREOF

This application claims priority from German patent applications number 19908752.0 filed 19 Feb. 1999 and number 19908766.0 filed 19 Feb. 1999.

SUMMARY

The invention pertains to synthetic (s) peptides derived from the viral regulatory protein R (Vpr) of the human immunodeficiency virus type 1 (HIV-1), particularly the chemical synthesis of the 96 amino acid full length Vpr protein, $sVpr^{1-96}$, as well as several fragments thereof. The application of those synthetic HIV-1 Vpr peptides in biological assays, for molecular and structural characterization, as well as for the development of anti-Vpr antibodies and serodiagnostic test systems are disclosed.

So far the only in vitro characterized biochemical activity of HIV-1 Vpr is that of a cation-selective ion channel (Piller et al., 1996, list of references at the end of examples). Those studies are based on the assumption that the C-terminal alpha-helix (amino acid position 46 to 71 in Vpr), which contains certain similarity to the honey bye poison melittin, has the capability to govern as a transmembrane anchor the formation of a membrane pore. Indeed, recombinant Vpr expressed in Escherichia (E.) coli was reconstituted in artificial planar lipid bilayers. Using this system, an ion channel activity was identified that is gated by the membrane potential. The gating of the channel is dependent on the positively charged C-terminal domain of Vpr which is believed to interact with the cytoplasmic part of the cell membrane.

There is evidence that Vpr forms homo oligomers: a recombinant Vpr-fusion protein was found in oligomeric structures of a molecular weight >100 kDa (Zhao et al., 1994b). So far, this observation could not be confirmed by studies on viral Vpr. The molecular structure of Vpr was investigated by two laboratories using analyses of the secondary structure on short Vpr-Peptides: alpha-helical regions in Vpr positions 50–82 was identified by NMR-studies on overlapping peptides in aqueous trifluorethanol (TFE) as well as in sodium dodecylsulfate (SDS)-micelles (Yao et al., 1998). The propensity for helix formation was predicted by several authors for regions within the C-terminus as well as the N-terminus of Vpr (Mahalingam et al., 1995a–d; Yao et al., 1995; Wang et al., 1996b). Recent studies on 25 amino acid long peptides using CD-spectroscopy in aqueous TFE solutions (Luo et al., 1998) provided first experimental evidence for the existence of N- and C-terminal helices in Vpr. Based on mutational analyses, numerous and, at least partial, contradictory information was reported that tried to correlate certain primary and secondary structures of Vpr with different biological activities reported for Vpr (Mahalingam et al., 1995a–d, 1997; Wang et al., 1996a,b; Nie et al., 1998; Di Marzio et al., 1995).

The chemical total synthesis of a Vpr peptide was first described 1997 by Rocquigny and colleagues. The authors reported the synthesis of a 96 amino acid long peptide derived from the virus isolate HIV-1$_{89.6}$ (Collman et al. 1992). Beside the disadvantages of this synthesis reported by the authors in their publication (see in the further text) this protein is different in nine amino acid positions compared to the Vpr protein derived from the virus isolate HIV-1$_{NL4-3}$, the synthesis of which is described for the first time in the present specification. As such, there is a 10% difference in the amino acid sequence between the already described (Rocquigny et al., 1997) and the synthetic products covering the entire as well as partial sequences of the Vpr protein derived from the virus isolate HIV-1$_{NL4-3}$ (Adachi et al., 1986) as described in detail in the present processes.

Rocquigny and colleagues (1997) did not reveal any information about the purity and the molecular characteristics of those synthetic Vpr peptides. The authors merely described far-Western blot techniques that demonstrate binding of SDS-denatured Vpr peptide with the viral nucleocapsid protein $p7^{NC}$ derived from the same HIV-1-isolate. So far, this observation of $p7^{NC}$-Vpr-interaction could not be repeated by any other of the numerous laboratories working worldwide in Vpr research. An important disadvantage of the Vpr synthesis described by Rocquigny and colleagues (1997) is the fact that none of the so far well-characterized biological functions of HIV-1 Vpr could be demonstrated by the authors for those synthetic peptides. Specifically, the authors show that this particular Vpr peptide does not bind to $p6^{Gag}$, a well recognized characteristic of native viral Vpr (Paxton et al., 1993; Lavallee et al., 1994; Kondo et al., 1995; Lu et al., 1995; Kondo and Göttlinger, 1996). In addition, the authors report that this Vpr peptide does not form oligomeric structures, and there are some indications that this synthetic product is insoluble in aqueous solutions. A model of Vpr-$p7^{NC}$-interaction was introduced by the same laboratory in an additional study based on structural analyses conducted on partial sequences of Vpr peptides, however, no detailed information about structural and experimental data were provided in this or other reports published by the authors (Roques et al., 1997).

Partial sequences of synthetic Vpr peptides (amino acid positions 50 to 75, 50 to 82, and 59 to 86) were used for NMR studies (Yao et al., 1998). Another group applied circular dichroism spectroscopy to investigated two 25 amino acid long peptides derived from the predicted alpha helical domains in Vpr (Luo et al., 1998). Furthermore, short approximately 20 amino acid long peptides derived from the C-terminal region of Vpr comprising the motif "HF/SRIG" at a concentration range of 0.7 to 3 micro-M had cytotoxic activity towards different yeast strains, for example Saccharomyces cerevisiae, Candida albicans and Schizosaccharomyces pombe (Macreadie et al., 1996, 1997). Elevated concentrations of bivalent cations, especially magnesium and calcium, prevented uptake and thus the toxic effects of Vpr-peptides. Continuing studies provided evidence that the C-terminal Vpr peptide (amino acid positions 71–82) can induce permeabilization of membranes, the reduction of membrane potential, and eventually cell death in CD4$^+$ T cells (Macreadie et al., 1997). Similar toxic effects were also for full length (Arunagiri et al., 1997). For those studies the same recombinant glutathione S-transferase (GST)-Vpr-fusion protein was used which was also employed for ion channel studies on Vpr before (Piller et al., 1996). Nevertheless, as in previous studies the authors reported problems with solubility of the recombinant product in aqueous systems.

Recombinant Vpr derived from the viral isolate HIV-1$_{NL4-3}$ was expressed in insect cells infected with recombinant baculoviruses (Levy et al., 1995). The purification of those products was merely conducted by immune affinity chromatography on immobilized polyclonal antibodies directed against the N-terminal domain of Vpr. For this procedures cell culture supernatants were applied as recombinant Vpr was secreted into the culture medium.

Strategies for large scale production of recombinant Vpr have not been described thus far. In most cases, cell culture supernatants containing recombinant Vpr were used for biological assays. In such an assay it was shown that recombinant Vpr activates virus replication in PBMC (peripheral blood mononuclear cells) as well as in several monocyte and T cell lines latently infected with HIV-1. Significant disadvantages of these already described methods are:

- low yield that does not allow production of mg-amounts of highly purified Vpr products;
- detergents were added to the recombinant Vpr during the process of affinity purification that required subsequent dialysis and renaturation;
- no studies about the potential of post translational modification of Vpr in insect cells were reported.

Expression, purification and biochemical characterization of recombinant Vpr was first described 1994 by Zhao and colleagues. For this procedure the coding sequence of Vpr protein derived from the virus isolate HIV-1$_{89.6}$ was expressed in *E. coli* as a fusion protein. For the purpose of purification of the recombinant product, the 25 amino acid FLAG epitope was fused on the C-terminus. Besides oligomerization, no biological activity was reported for this recombinant product. A significant disadvantage of this method is the fact that Vpr is not expressed in its authentic sequence, but as a fusion protein.

In another procedure, Vpr protein derived from the virus isolate HIV-1$_{HXB2}$ was expressed in *E. coli* as a GST-fusion protein (Piller et al., 1996). After affinity chromatography on glutathione-agarose, Vpr was released from the fusion protein by proteolytic cleavage with thrombin. A significant disadvantage of the method is the fact that Vpr after thrombin cleavage tends to aggregate and could not be sustained in aqueous solution. It was reported by Arunagiri and colleagues (1997) that Vpr produced with this method could not be maintained in aqueous solution without protein precipitation and aggregation following cleavage of the GST fusion part, while only the GST-Vpr fusion protein was usable for test systems in aqueous solutions.

The patent application WO 95/26361 (Azad, A. A., Macreadie, I. G., Arunagiri, C., 1995) describes biologically active peptide fragments of HIV Vpr proteins; pharmaceutical compounds that contain those peptides or biologically active analogs thereof; antagonists of Vpr-peptides as well as pharmaceutical compounds that contain such Vpr-antagonists. The chemical synthesis of full length Vpr is not described in this method.

The patent application WO 96/07741 (Cohen, E.; Bergeron, D.; Checroune, F.; Yao, X. -J.; Pignac-Kobinger, G., 1996) protects chimeric molecules consisting of Vpr from HIV-1 and Vpx from HIV-2 that are specifically incorporated in HIV-1/HIV-2 virus particles and there interfere with the structure and function of budding virions Those chimeric molecules are protected for the application in gene therapy of HIV-1/HIV-2 infections.

The patent application WO 96/08970 (Weiner, D. B.; Levy, D. N.; Refaeli, Y., 1996) describes methods to block cell division lymphocyte activation using Vpr proteins, fragments of Vpr or sequences of vpr genes. The chemical synthesis of Vpr proteins is not described in this method.

The application of vpr genes in screening assay for anti-HIV-pharmaceuticals is described in U.S. Pat. Nos. 5,721,104 and 5,639,619, for determination of HIV-2 infection in U.S. Pat. No. 5,580,739, a Vpr-receptor-protein is described in U.S. Pat. No. 5,780,238.

The invention is based on the need to develop a protocol for the high yield synthesis of Vpr proteins in mg-amounts, the purification of those Vpr proteins, and so that the end product, the highly purified Vpr proteins, can made available for general usage.

According to the invention, the problem is solved by the provision of the protein sVpr$^{1-96}$ as well as the following peptides:

- a forty seven amino acid long N-terminal peptide (sVpr$^{1-47}$),
- a forty nine amino acid long C-terminal peptide (sVpr$^{48-96}$) and fragments of those peptides thereof, for example:
- overlapping approximately fifteen amino acid long peptides for the purpose of epitope mapping and isoelectric focusing;
- approximately twenty amino acid long peptides for the structural and functional characterization of individual domains in Vpr, particularly the peptides sVpr$^{1-20}$ and sVpr$^{21-40}$:

sVpr$^{1-96}$:

H-Met-Glu-Gln-Ala-Pro-Glu-Asp-Gln-Gly-Pro-Gln-Arg-Glu-Pro-Tyr-Asn-Glu-Trp-Thr-Leu-Glu-Leu-Leu-Glu-Glu-Leu-Lys-Ser-Glu-Ala-Val-ARg-His-Phe-Pro-Arg-Ile-Trp-Leu-His-Asn-Leu-Gly-Gln-His-Ile-Tyr-Glu-Thr-Tyr-Gly-Asy-Thr-Trp-Ala-Gly-Val-Glu-Ala-Ile-Arg-Ile-Leu-Gln-Gln-Leu-Leu-Phe-Ile-His-Phe-Arg-Ile-Gly-Cys-Arg-His-Ser-Arg-Ile-Gly-Val-Thr-Arg-Gln-Arg-Arg-Ala-Arg-Asn-Gly-Ala-Ser-Arg-Ser-OH (SEQ ID NO: 1)

sVpr$^{1-47}$:

H-Mer-Glu-Gln-Ala-Pro-Glu-Asp-Gln-Gly-Pro-Gln-Arg-Glu-Pro-Tyr-Asn-Glu-Trp-Thr-Leu-Glu-Leu-Leu-Glu-Glu-Leu-Lys-Ser-Glu-Ala-Val-Arg-His-Phe-Pro-Arg-Ile-Trp-Leu-His-Asn-Leu-Gly-Gln-His-Ile-Try-NH$_2$ (SEQ ID NO: 2)

sVpr$^{48-96}$:

Glu-Thr-Tyr-Gly-Asp-Thr-Trp-Ala-Gly-Val-Glu-Ala-Ile-Ile-Arg-Ile-Leu-Gln-Gln-Leu-Leu-Phe-Ile-His-Phe-Arg-Ile-Gly-Cys-Arg-His-Ser-Arg-Ile-Gly-Val-Thr-Arg-Gln-Arg-Arg-Ala-Arg-Asn-Gly-Ala-Ser-Arg-Ser-OH (SEQ ID NO: 3)

sVpr$^{1-20}$ as mutant sVpr$^{1-20}$(Asn$^{5,10,14}$):

H-Mer-Glu-Gln-Ala-Asn-Glu-Asp-Gln-Gly-Asn-Gln-Arg-Glu-Asn-Tyr-Asn-Glu-Tsp-Thr-Leu-NH$_2$ (SEQ ID NO: 8), and sVpr$^{21-40}$ as mutant sVpr$^{21-40}$ (Asn$^{35}$):

H-Glu-Leu-Leu-Glu-Glu-Leu-Lys-Ser-Glu-Ala-Val-Arg-His-Phe-Asn-Arg-Ile-Trp-Leu-His-NH$_2$ (SEQ ID NO: 9), fragments of those peptides comprising approximately fifteen amino acid long peptides, sVpr$^{11-25}$:

H-Gln-Arg-Glu-Pro-Tyr-Asn-Glu-Trp-Thr-Leu-Glu-Leu-Leu-Glu-Glu-NH$_2$ (SEQ ID NO: 4), sVpr$^{41-55}$:

H-Asu-Leu-Gly-Gln-His-Ile-Tyr-Glu-Thr-Tyr-Gly-Asp-Thr-Trp-Ala-NH$_2$ (SEQ ID NO: 5), sVpr$^{46-60}$:

H-Ile-Tyr-Glu-Thr-Tyr-Gly-Asp-Thr-Trp-Ala-Gly-Val-Glu-Ala-Ile-NH$_2$ (SEQ ID NO: 6), sVpr$^{56-70}$:

H-Gly-Val-Glu-Ala-Ile-Ile-Arg-Ile-Leu-Gln-Gln-Leu-Leu-Phe-Ile-NH$_2$ (SEQ ID NO: 7), sVpr$^{66-80}$:

H-Gln-Leu-Leu-Phe-Ile-His-Phe-Arg-Ile-Gly-Cys-Arg-His-Ser-Arg-NH$_2$ (SEQ ID NO: 10), sVpr$^{76-96}$:

H-Cys-Arg-His-Ser-Arg-Ile-Gly-Val-Thr-Arg-Gln-Arg-Arg-Ala-Arg-Asn-Gly-Ala-Ser-Arg-Ser-OH (SEQ ID NO: 11).

The C-terminal Vpr-peptide was synthesized on a serine resin using a Perkin-Elmer-peptide synthesizer. All N-terminal peptides were synthesized on a polystyrene-polyoxyethylen-resin. The chain elongation was performed using the FMOC (Fluormethyloxycarbonyl)-strategy using certain protection groups. At the end of the synthesis the cleavage of the protection groups was performed using a cleavage solutions consisting of 95% trifluoro acetic acid (TFA), 3% triisopropylsilane and 2 to 5% ethanedithiol, depending on the peptide length synthesized. The resin was removed, the reaction mixture was concentrated and heptane was added. Following concentration the remaining oil was digested with diethyl ether. The raw peptide was removed and lyophilized in acetic acid. Purification of the raw peptide was performed on a preparative HPLC-system (High Pressure Liquid Chromatography). All peptides were purified on a column of silica gel using a linear gradient of TFA and water in acetonitrile. The eluated peptides were concentrated and lyophilized.

Surprisingly, it was found that in contrast to previously described recombinant and synthetic Vpr products, even at mM concentration sVpr-peptides are very soluble in water and remain stable without any sign of protein aggregation and protein precipitation following the described purification protocol in accordance with the invention.

It was demonstrated that the peptide sVpr$^{1-96}$ adopts a folded structure, is immunologically reactive and possess biological activities comparable to native viral Vpr.

For the first time the chemical synthesis of Vpr-proteins and fragments thereof are described which comprise amino acid sequence of the virus isolate HIV-1$_{NL4-3}$. The term synthetic (s) Vpr-peptides within the scope of the present specification illustrates those peptides synthesized by solid phase peptide synthesis which comprises the authentic amino acid sequence of the native Vpr-Proteins encoded by the vpr gene derived from the molecular virus isolates HIV-1$_{NL4-3}$.

The essence of the invention lies within the combination of already known characteristics (starting materials, synthesis resin, peptide synthesizer) and novel solutions, the first chemical synthesis of those compounds, the synthesis strategy, the specific protection groups, the cleavage resin trifluoroacetic acid-triisopropylsilane-ethanedithiole according to the invention, the application of certain gradients of solvents (TFA-water:TFA-acetonitrile) for the purpose of purification of peptides,—which are mutually influential and result in their entire action in an advantage of use and the desired success, in that synthetic sVpr-peptides are now available.

The according to the invention synthesized peptides are characterized by the following uniqueness:

They are extremely well soluble in aqueous systems enabling for the first time peptide concentrations as high as in the mM concentration range. This in turn is an essential prerequisite for following structural analysis using NMR (nuclear magnetic resonance)-spectroscopy and X-ray crystallography.

The peptides can be produced in mg amounts under economically reasonable conditions and can be purified to the highest standard. The biological characteristics and immunological reactivity of the peptides are identical to that of the native viral Vpr proteins. The peptides can be used for a variety of applications in the basic research as well as in the applied research in areas of HIV virology.

The peptides according to the invention are used in biological assays, in structural analyses of Vpr and domains thereof, for the generation of antibodies directed against HIV peptide sequences, in anti-viral reagents, for the generation of test systems for the screening of potential Vpr inhibitors, for establishment of cell culture and animal models, for the investigation of mechanisms of Vpr in HIV pathology, for in vitro assembly of HIV, for generation of novel vectors in gene therapy, and for the development of serological assays, specifically a Vpr capture ELISA (enzyme linked immune solvent assay).

The created products according to the invention can be used for the determination of the molecular structure of Vpr using NMR- and CD spectroscopy as well as X-ray crystallography. Those structural information in turn are essential for understanding the molecular mechanism of Vpr proteins in the HIV replication cycle and their role in pathological mechanism involved in AIDS related diseases. Furthermore, those products can be used for the development and the design of high throughput in vitro test systems to search for potential Vpr inhibitors as well as for the generation and characterization of Vpr specific antibodies and serological test systems.

The invention will be used in areas like peptide chemistry, basic research in virology, structural analyses, and medical diagnosis. The invention can be used for the generation of poly- and monoclonal Vpr specific antibodies, specifically for the generation of epitope different Vpr specific antibodies. Further areas of application are: serological test systems, specifically Vpr antigen (Ag) ELISA, as standard antigen for calibration of Vpr-Ag ELISA-techniques, for detection and quantitation of viral Vpr in blood samples of HIV infected individuals, for test systems that characterize Vpr inhibitors, for complementation of the function of endogenous viral Vpr in cultured cells infected with vpr-deficient HIV mutants, for complementation of the function of viral Vpr in cultures of human lymphocytes infected with vrp-deficient HIV-mutants and for complementation of the function of viral Vpr in cultures of differentiated human monocytes/macrophages infected with vpr-deficient HIV-mutants.

The invention can be used for the characterization of reagents that:
a) block the interaction of Vpr with cellular factors, like for the glucocorticoid-receptor, transcription factors and other DNA interacting enzymes and factors;
b) regulate or block the transcription-activating function of Vpr and the activity of Vpr on steroid hormones;
c) regulate or block the transport of Vpr alone, or in conjunction with components of the HIV-pre-integration complex, and the incorporation of Vpr into budding virions during virus assembly;
d) regulate or block the Vpr-induced cell cycle arrest, and the effect of Vpr on cell differentiation and cell growth;
e) regulate or block the cytotoxic effect of Vpr, and
f) regulate or block the ion channel activity of Vpr.

Furthermore, the invention allows the application in the development and design of in vivo test systems for the characterization of Vpr inhibitors and animal studies. Another advantage is that with this invention for the first time concentrated solution of Vpr can be generated for molecular, structural and function analyses necessary for the design of Vpr specific inhibitors. Another application of the invention is the reduction of the flexibility of Vpr's N-terminus using structure stabilizing factors like the UBA2- domain of the DNA repairing enzyme HHR23A which binds to Vpr, Fab-fragments derived from Vpr-specific immune globulins or viral factors, specifically components of the HIV-1 Gag polypeptide precursor Pr55$^{Gag}$ which interact with Vpr during virus assembly, the human glucocorticoid receptor or components thereof. The invention support studies on the in vitro assembly of retroviral pre-integration complex, the development of in vitro and/or in vivo applicable methods of gene transfer, DNA transfection, integration into chromosomal and episomal host DNA, or other methods of gene transfer into cells, tissues or complete organisms with the purpose of gene therapeutic application.

The following Examples serve to explain the invention, without being limited thereto.

EXAMPLES

Example 1

Synthesis of Vpr-Peptides-General Protocol

Synthesis of the C-terminal Vpr-peptides was conducted using a ABI 433A synthesizer (Perkin Elmer) and a serine-resin provided by the company Fa. Rapp Polymere, Tübinger, Germany. All N-terminal Vpr peptides were synthesized on a polystyrene-polyoxyethylen-resin, "TentaGel R-RAM-resin" provided by the company Fa. Rapp Polymere, Tübingen, Germany. Synthesis of peptides was performed using the FMOC (fluoromethyloxycarbonyl)-strategy using the following protection groups: O-t.butylester for glutamate and asparagine, OtBu-ether for serine, tyrosine and threonine, Boc (tert-butoxycarbonyl-) for lysine and tryptophan, Trt (trityl-triphenylmethyl-) for histidine, glutamine and asparagine, and Pbf (2.2.4.6.7-pentamethyl-dihydrobenzofuran-5-sulfonyl-) for arginine. After finishing the synthesis cleavage of the protection groups was conducted using a mixture consisting of 95% trifluroracetic acid, 3% triisopropylsilane, and 2 to 5% ethanedithiol, depending on the specific peptide sequence. The resin was removed, the reaction mixture was concentrated and heptane was added. Following concentration the remaining oil was digested with diethyl ether. The raw peptide was removed and lyophilized in 10% acetic acid.

Example 2

Purification of Peptides-General Protocol:

100 mg of the raw peptide was purified by preparative HPLC using the Shimadzu LC-8 system. All peptides were purified on a column (300×400 mm Vydac-RP18-Säule, grain size 15–20 μM) containing column of silica gel. A linear gradient consisting of 1% TFA (trifluor acetic acid) in water 0, 1% TFA in 80% acetonitrile was applied with a flow rate of 100 ml/min. Eluted peptides were concentrated and lyophilized.

Example 3 sVpr$^{1-96}$

The peptide was synthesized on a TentaGel S-AC-resin (0.20 mmol/gram) using an ABI 433 synthesizer. At the end of the synthesis procedure, FMOC-protection groups were cleaved off and the resin was washed first with dimethylformamide and methylenchloride and then dried. The peptide was removed from the resin and purified as described above. molecular weight: calculated: 11378 found: 11381

H-Met-Glu-Gln-Ala-Pro-Glu-Asp-Gln-Gly-Pro-Gln-Arg-Glu-Pro-Tyr-Asn-Gln-Trp-Thr-Leu-Glu-Leu-Leu-Glu-Glu-Leu-Lys-Ser-Glu-Ala-Val-Arg-His-Phe-Pro-Arg-Ile-Trp-Leu-His-Asn-Leu-Gly-Gln-His-Ile-Tyr-Glu-Thr-Tyr-Gly-Asp-Thr-Trp-Ala-Gly-Val-Glu-Ala-Ile-Ile-Arg-Ile-Leu-Gln-Gln-Leu-Leu-Phe-Ile-His-Phe-Arg-Ile-Gly-Cys-Arg-His-Ser-Arg-Ile-Gly-Val-Thr-Arg-Gln-Arg-Arg-Ala-Arg-Asn-Gly-Ala-Ser-Arg-Set-OH (SEQ ID NO: 1).

Figure 2:
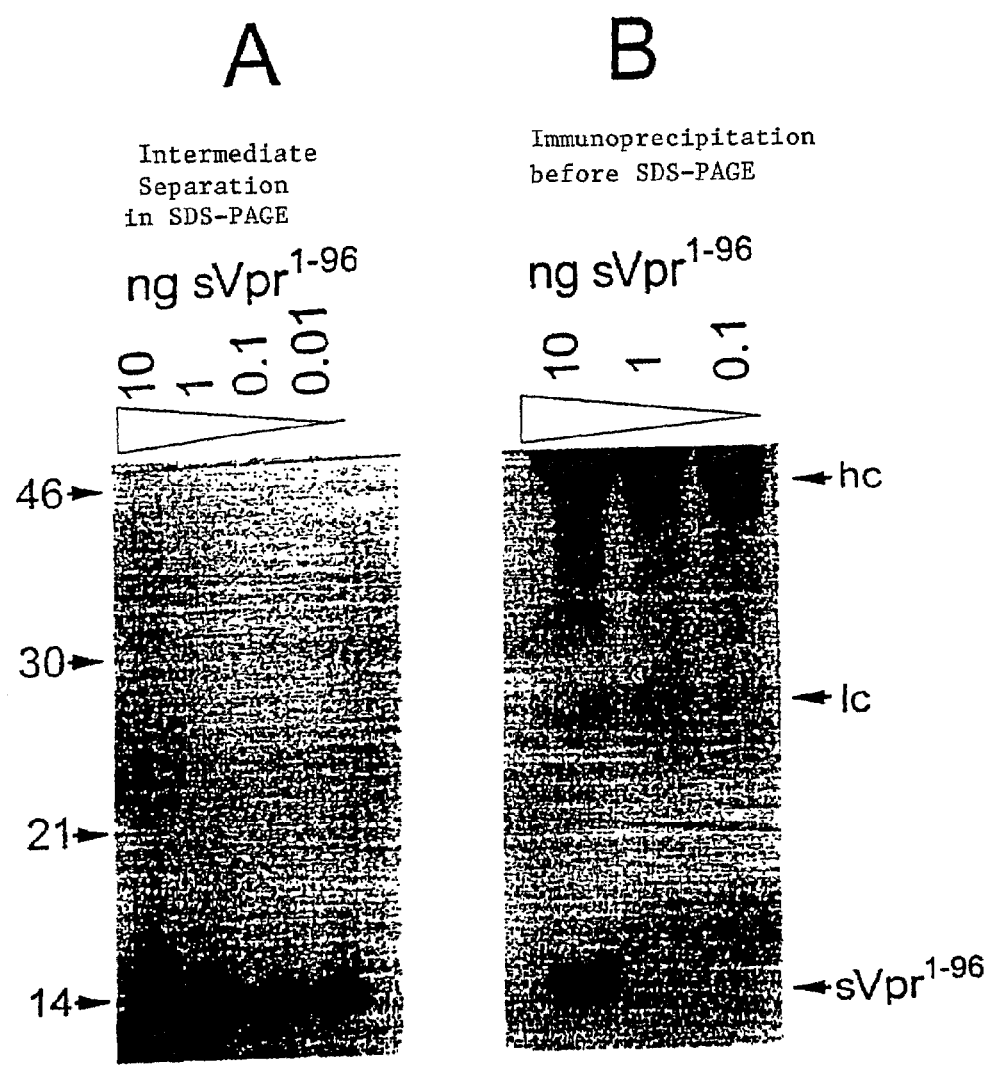

FIG. 2: sVpr$^{1-96}$—direct separation in SDS-PAGE (A); immune precipitation prior to SDS-PAGE (B).

Figure 7:
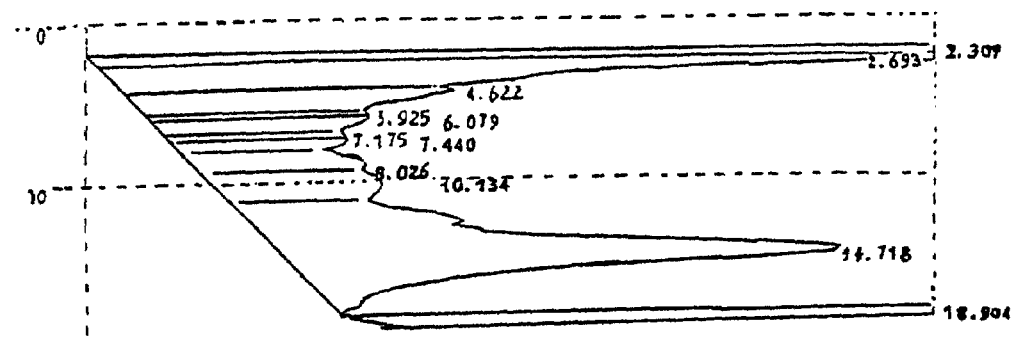
Figure 7:
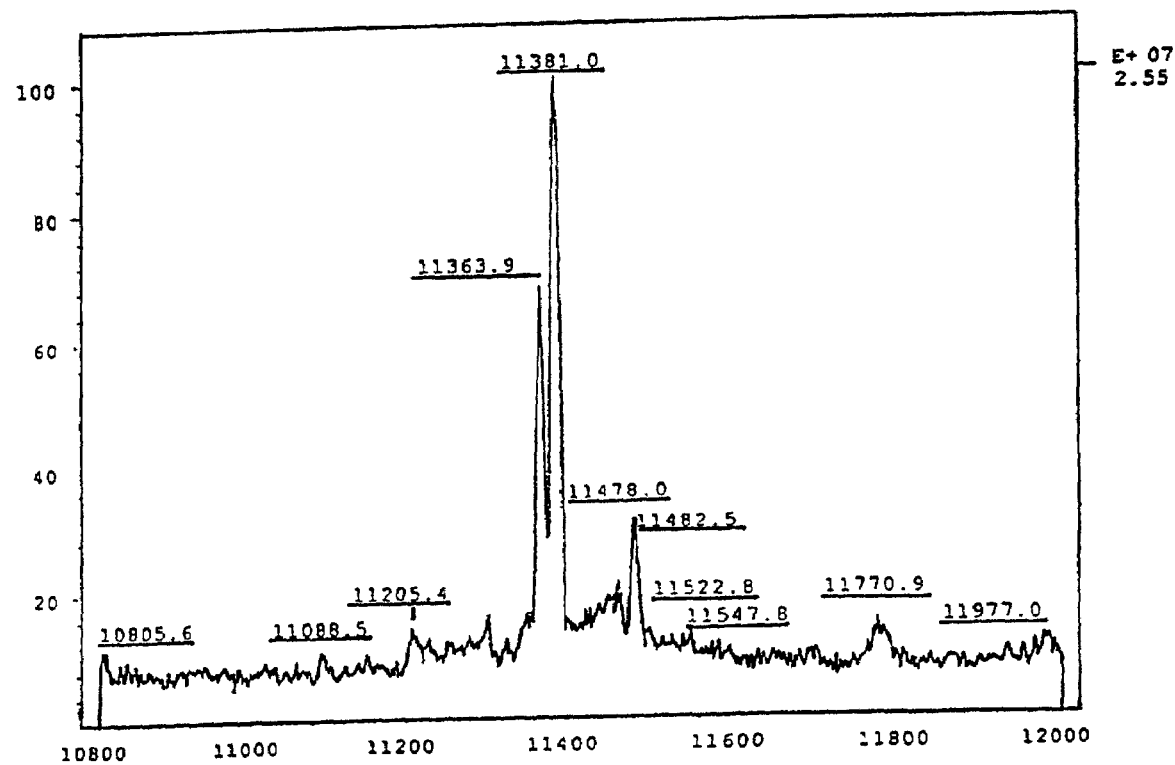

FIG. 7: sVpr$^{1-96}$—preparative purification of the raw—HPLC-chromatogram.

Figure 3:
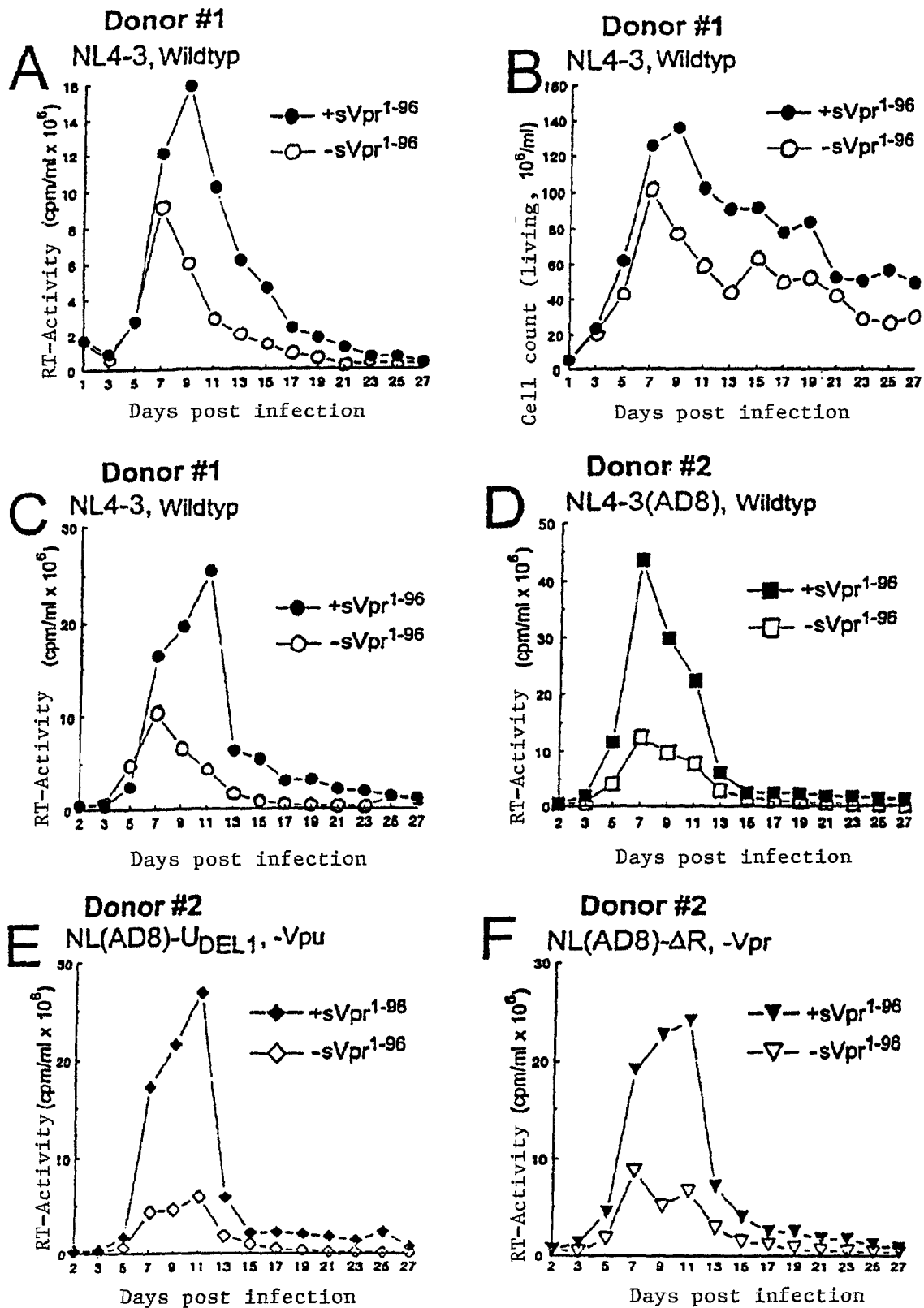

FIG. 3: sVpr$^{1-96}$—mass spectrum (% int. and molecular weight).

Example 4 sVpr$^{1-47}$ in analogy to examples 1 to 3. molecular weight: calculated: 5728 found: 5728.8

H-Met-Glu-Gln-Ala-Pro-Glu-Asp-Gln-Gly-Pro-Gln-Arg-Glu-Pro-Tyr-Asn-Glu-Trp-Thr-Leu-Glu-Leu-Leu-Glu-Glu-Leu-Lys-Ser-Glu-Ala-Val-Arg-His-Phe-Pro-Arg-Ile-Trp-Leu-His-Asn-Leu-Gly-Gln-His-Ile-Tyr-NH$_2$ (SEQ ID NO: 9).

Example 5 sVpr$^{48-96}$ in analogy to examples 1 to 3.

Glu-Thr-Tyr-Gly-Asp-Thr-Trp-Ala-Gly-Val-Glu-Ala-Ile-Ile-Arg-Ile-Leu-Gln-Gln-Leu-Leu-Phe-Ile-His-Phe-Arg-Ile-Gly-Cys-Arg-His-Ser-Arg-Ile-Gly-Val-Thr-Arg-Gln-Arg-Arg-Ala-Arg-Asn-Gly-Ala-Ser-Arg-Ser-OH (SEQ ID NO: 3).

Example 6 sVpr$^{1-20}$ in analogy to examples 1 to 3.

H-Met-Glu-Gln-Ala-Pro-Glu-Asp-Gln-Gly-Pro-Gln-Arg Glu-Pro-Tyr-Asn-Glu-Trp-Thr-Leu-NH$_2$ (SEQ ID NO: 8).

Figure 5:
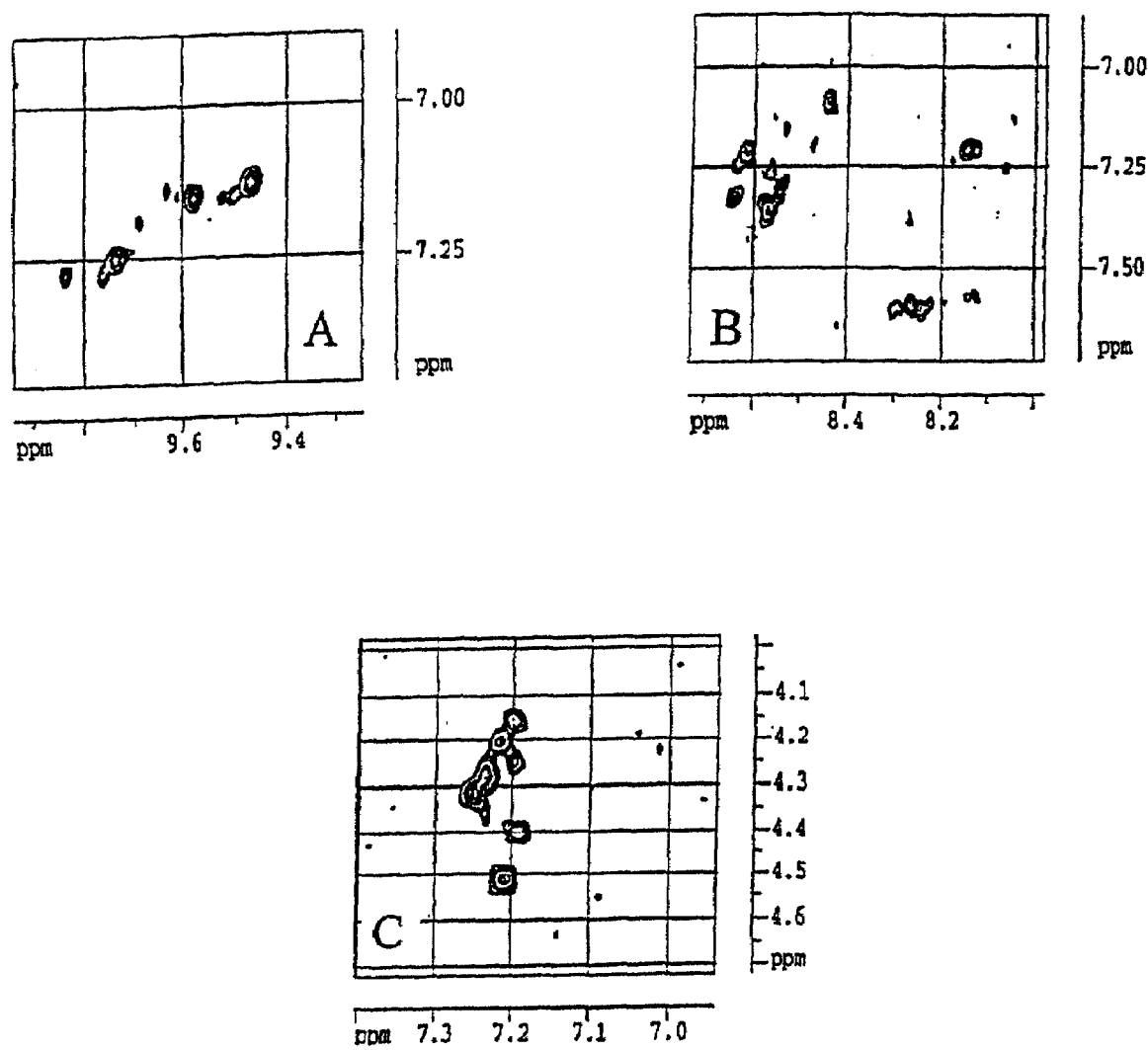

FIG. 5: sVpr$^{1-20}$—mass spectrum (% int. and molecular weight) (% Int. 10%=111 mV[sum=9505 mV].

Example 7 sVpr$^{1-20}$(Asn$^{5,10,14}$) in analogy to examples 1 to 3.

H-Met-Glu-Gln-Ala-Pro-Glu-Asp-Gln-Gly-Pro-Gln-Arg Glu-Pro-Tyr-Asn-Glu-Trp-Thr-Leu-NH$_2$ (SEQ ID NO: 8).

Example 8 sVpr$^{21-40}$ in analogy to examples 1 to 3. Wildtype-sequence:

H-Glu-Leu-Leu-Glu-Glu-Leu-Lys-Ser-Glu-Ala-Val-Arg-His-Phe-Asn-Arg-Ile-Trp-Leu-His-NH$_2$ (SEQ ID NO: 9).

Example 9 sVpr$^{21-40}$(Asn$^{35}$) in analogy to examples 1 to 3.

H-Glu-Leu-Leu-Glu-Glu-Leu-Lys-Ser-Glu-Ala-Val-Arg-His-Phe-Asn-Arg-Ile-Trp-Leu-His-NH$_2$ (SEQ ID NO: 9).

Example 10 sVpr$^{11-25}$: in analogy to examples 1 to 3.

H-Gln-Arg-Glu-Pro-Tyr-Asn-Glu-Trp-Thr-Leu-Glu-Leu-Leu-Glu-Glu-NH$_2$ (SEQ ID NO: 4).

Example 11 sVpr$^{41-55}$: in analogy to examples 1 to 3.
H-Asn-Leu-Gly-Gln-His-Ile-Tyr-Glu-Thr-Tyr-Gly-Asp-Thr-Trp-Ala-NH$_2$ (SEQ ID NO: 5).

Example 12 sVpr$^{46-60}$: in analogy to examples 1 to 3.
H-Ile-Tyr-Glu-Thr-Tyr-Gly-Asp-Thr-Trp-Ala-Gly-Val-Glu-Ala-Ile-NH$_2$ (SEQ ID NO: 6).

Example 13 sVpr$^{56-70}$: in analogy to examples 1 to 3.
H-Gly-Val-Glu-Ala-Ile-Ile-Arg-Ile-Leu-Gln-Gln-Leu-Leu-Phe-Ile-NH$_2$ (SEQ ID NO: 7).

Example 14 sVpr$^{66-80}$: in analogy to examples 1 to 3.
H-Gln-Leu-Leu-Phe-Ile-His-Phe-Arg-Ile-Gly-Cys-Arg-His-Ser-Arg-NH$_2$ (SEQ ID NO: 10).

Example 15 sVpr$^{76-96}$ in analogy to examples 1 to 3.
H-Cys-Arg-His-Ser-Arg-Ile-Gly-Val-Thr-Arg-Gln-Arg-Arg-Ala-Arg-Asn-Gly-Ala-Ser-Arg-Ser-OH (SEQ ID NO: 11).

Literature:

Adachi, A.; Gendelman, H. E.; König, S.; Folks, T.; Willey, R. L.; Rabson, A.; Martin, M. A. (1986) Production of acquired immunodeficiency syndrome-associated retrovirus in human and non-human cells transfected with an infectious molecular clone. J. Virol. 59:284–291.

Arunagiri, C.; Macreadie, I; Hewish, D.; Azad, A. (1997) A C-terminal domain of HIV-1 accessory protein Vpr is involved in penetration, mitochondrial dysfunction and apoptosis of human CD4+ lymphocytes. Apoptosis 2:69–76.

Collman, J. W.; Balliet, J. W.; Greory, S. A.; Friedman, H.; Kolson, D. L; Nathanson, N.; Srinivasan, A. (1992) An infectious molecular clone of an unusual macrophage-tropic and highly cytopathic strain of human immunodeficiency virus type 1. J. Virol. 66:5717–5721.

Di Marzio, P.; Choe, S.; Ebright, M.; Knoblauch, R.; Landau, N. R. (1995) Mutational analysis of cell cycle arrest, nuclear localization and virion packaging of human immunodeficiency virus type 1 Vpr. J. Virol. 69:7909–7916.

Kondo, E.; Göttlinger, H. G. (1996) A conserved LXXLF sequence is the major determinant in p6gag required for the incorporation of human immunodeficiency virus type 1 Vpr. J. Virol. 70:159–164.

Kondo, E.; Mammano, F.; Cohen, E. A.; Göttlinger, H. G. (1995) The p6gag domain of human immunodeficiency virus type 1 is sufficient for incorporation of Vpr into heterologous viral particles. J. Virol. 69:2759–2764.

Lavallée, C.; Yao, X. J.; Ladha, A.; Göttlinger, H. G.; Haseltine, W. A.; Cohen, E. A. (1994) Requirement of the pr55gag precursor for incorporation of the Vpr product into human immunodeficiency virus type 1 viral particles. J. Virol. 68:1926–1934.

Levy, D. N.; Refaeli, Y.; Weiner, D. B. (1995) Extracellular Vpr protein increases cellular permissiveness to human immunodeficiency virus type 1. Proc. Natl. Acad. Sci. USA 91:10873–10877.

Lu, Y. -L., Bennett, R. P.; Wills, J. W.; Gorelick, R.; Ratner, L. (1995) A leucine triplet repeat sequence (LXX)4 in p6gag is important for Vpr incorporation into human immunodeficiency virus type 1 particles. J. Virol. 69:6873–6879.

Luo, Z.; Butcher, D. J.; Murali, R.; Srinivasan, A.; Huang, Z. (1998) Structural studies of synthetic peptide fragments derived from the HIV-1 Vpr protein. Biochem. Biophys. Research Communications 244:732–736.

Macreadie, I. G.; Arunagiri, C. K.; Hewish, D. R.; White, J. F.; Azad, A. A. (1996) Extracellular addition of a domain of HIV-1 Vpr containing the amino acid sequence motif H(S/F)RIG causes cell membrane permeabilization and death. Mol. Microbiol. 19:1185–1192.

Macreadie, I. G.; Kirkpatrick, A.; Strike, P. M.; Azad, A. A. (1997) Cytocidal activities of HIV-1 Vpr and SAC1P peptides bioassayed in yeast. Protein and Peptide Letters 4:181–186.

Mahalingam, S.; Ayyavoo, V.; Patel, M.; Kieber-Emmons, T.; Weiner, D. B. (1997) Nuclear import, virion incorporation, and cell cycle arrest/differentiation are mediated by distinct functional domains of human immunodeficiency virus type 1 Vpr. J. Virol. 71:6339–6347.

Mahalingam, S.; Collman, R. G.; Patel, M.; Monken, C. E.; Srinivasan, A. (1995a) Functional analysis of HIV-1 Vpr: Identification of determinants essential for subcellular localization. Virol. 212:331–339.

Mahalingam, S.; Khan, S. H.; Jabbar, M. A.; Monken, C. E.; Collman, R. G.; Srinivasan, A. (1995b) Identification of residues in the N-terminal acidic domain of HIV-1 Vpr essential for virion incorporation. Virol. 207:297–302.

Mahalingam, S.; Kahn, S. H.; Murali, R.; Jabbar, M. A.; Monken, C. E.; Collman, R. G.; Srinivasan, A. (1995c) Mutagenesis of the putative alpha-helical domain of the Vpr protein of human immunodeficiency virus type 1: effect on stability and virion incorporation. Proc. Natl. Acad. Sci. USA 92:3794–3798.

Mahalingam, S.; Patel, M.; Collman, R. G., Srinivasan, A. (1995d) The carboxy terminal domain is essential for stability and not for virion incorporation of HIV-1 Vpr into virus particles. Virol. 214:647–652.

Nie, Z.; Bergeron, D.; Subbramanian, R. A.; Yao, X. -J.; Checroune, F.; Rougeau, N.; Cohen, E. A. (1998) The putative alpha helix 2 of human immunodeficiency virus type 1 Vpr contains a determinant which is responsible for the nuclear translocalization of proviral DNA in growth-arrested cells. J. Virol. 73:4104–4115.

Paxton, W.; Connor, R. I.; Landau, N. R. (1993) Incorporation of vpr into human immunodeficiency virus type 1 virions: requirement for the p6 region of gag and mutational analysis. J. Virol. 67:7229–7237.

Piller, S. C.; Ewart, G. D.; Premkumar, A.; Cox, G. B.; Gage, P. W. (1996) Vpr protein of human immunodeficiency virus type 1 forms cation-selective channels in planar lipid bilayers. Proc. Natl. Acad. Sci. USA 93:111–115.

Roques, B. P.; Morellet, N.; de Rocquigny, H.; Déméné, H.; Schueler, W.; Jullian, N. (1997) Structure, biological functions and inhibition of the HIV-1 proteins Vpr and NCp7. Biochimie 79:673–680.

de Rocquigny, H.; Petitjean, P.; Tanchou, V.; Decimo, D.; Drouot, L.; Delaunay, T.; Darlix, J. -L.; Roques, B. P. (1997) The zinc fingers of HIV nucleocapsid protein NCp7 direct interactions with the viral regulatory protein Vpr. J. Biol. Chem. 272(49):30753–30759.

Wang, B.; Ge, Y. C.; Palasanthiran, P.; Xiang, S. -H.; Ziegler, J.; Dwyer, D. E.; Randle, C.; Dowton, D.; Cunningham, A.; Saksena, N. K. (1996) Gene defects clustered at the C-terminus of the vpr gene of HIV-1 in long-term non-progressing mother and child pair: in vivo evolution of vpr quasispecies in blood and plasma. Virol. 223:224–232.

Wang, L.; Mukherjee, S.; Narayan, O; Zhao, L. -J. (1996) Characterization of a leucine-zipper-like domain in Vpr protein of human immunodeficiency virus type 1. Gene 178:7–13.

Yao, S.; Azad, A. A.; Macreadie, I. G.; Norton, R. S. (1998) Helical structure of polypeptides from the C-terminal half of HIV-1 Vpr. Protein and Peptide Letters 5:127–134.

Yao, X. -J.; Subbramanian, R. A.; Rougeau, N; Boisvert, F.; Bergeron, D.; Cohen, E. A. (1995) Mutagenic analysis of human immunodeficiency virus type 1 Vpr: role of a predicted N-terminal alpha-helical structure in Vpr nuclear localization and virion incorporation. J. Virol. 69:7032–7044.

Zhao, L. J.; Mukherjee, S.; Narayan, O. (1994a) Biochemical mechanism of HIV-1 Vpr function: specific interaction with a cellular protein. J. Biol. Chem. 269:15577–15582.

Zhao, L. J.; Wang, L.; Mukherjee, S.; Narayan, O. (1994b) Biochemical mechanism of HIV-1 Vpr function: oligomerization by the N-terminal domain. J. Biol. Chem. 269:32131–32137.

Zhao, Y.; Cao, J.; O'Gorman, M. R.; Yu, M.; Yogev, R. (1996) Effect of human immunodeficiency virus type 1 protein R (vpr) gene expression on basic cellular function of fission yeast *Schizosaccharomyces pombe*. J. Virol. 70:5821–5826.

Figure Legends:

FIG. 1: Structural and functional domains in Vpr

The following primary and secondary structural motifs are aligned to the amino acid sequence of the Vpr protein derived from the Isolate HIV-1$_{NL4-3}$: The negatively charged N-terminus (label (1), positions 1–17); helix alpha-1 (Label (2), positions 18–37); a not further defined region (label (3), positions 38–51); helix alpha-2 (label (4), positions 51–76); a positively charged C-terminus (label (8), positions 77–96). Overlapping to labels (1) to (5) and (87) the following domains are indicated: a leucine- and isoleucine-rich regions termed as "leucine-zipper-like or "LR-domain" (label (5), positions 60–80); a region containing the repetitive motif "HF/SRIG" (label (6), positions 71–82), the predicted transmembrane anchor of Vpr required for the ion channel activity of Vpr (label (7), positions 52–79).

FIG. 2: Immunological characterization of polyclonal antibodies specific for sVpr$^{1-96}$ by Western blot and immune precipitation.

Rabbits were immunized with sVpr$^{1-96}$ and the resulting serum R-96 was tested in Western blot (A) and immune precipitation (B). A serial dilution of sVpr$^{1-96}$, 0.01 to 10 ng, was separated in a SDS-PAGE (12.5% acryl aide gel) (A). A similar serial dilution of sVpr$^{1-96}$ was added to human serum and from the mixture sVpr$^{1-96}$ was recovered by immune precipitation using the serum R-96 followed by separation of the immune precipitates in a SDS-PAGE (B). sVpr$^{1-96}$ was electro-transferred onto PVDF-membranes and the peptide was detected using R-96 followed by binding to $^{125}$I-labeled protein G. The autoradiogram of a two-day exposure is shown in (A) and (B). Positions of the molecular weight standard proteins are indicated on the left, positions of the light (lc) and heavy chain (hc) of immune globulins used for immune precipitation are indicated on he right.

FIG. 3: sVpr$^{1-96}$ activates virus replication and increases the number of live cells in cultures of human PBMC.

Cultures of PHA- and IL-2-activated PBMCs were infected with equal infectious doses of the following virus stocks: HIV-1$_{NL4-3}$ (A, B, C), NL4-3(AD8) (D) as well as the vpu-deficient mutant NL(AD8)-U$_{DEL1}$ (E), and the vpr-deficient mutant NL(AD8)deltaR (F). During the course of the experiment cultures were incubated with 10 nM of sVpr$^{1-96}$ or 10 nM of the control peptide Vpu$^{32-81}$. Virus release is demonstrated as the profile of virus associated RT-activity released into the cell culture supernatant (A,C, D,E,F). (B) shows the number of live cells detected in the cultures of experiment (A).

Figure 4:
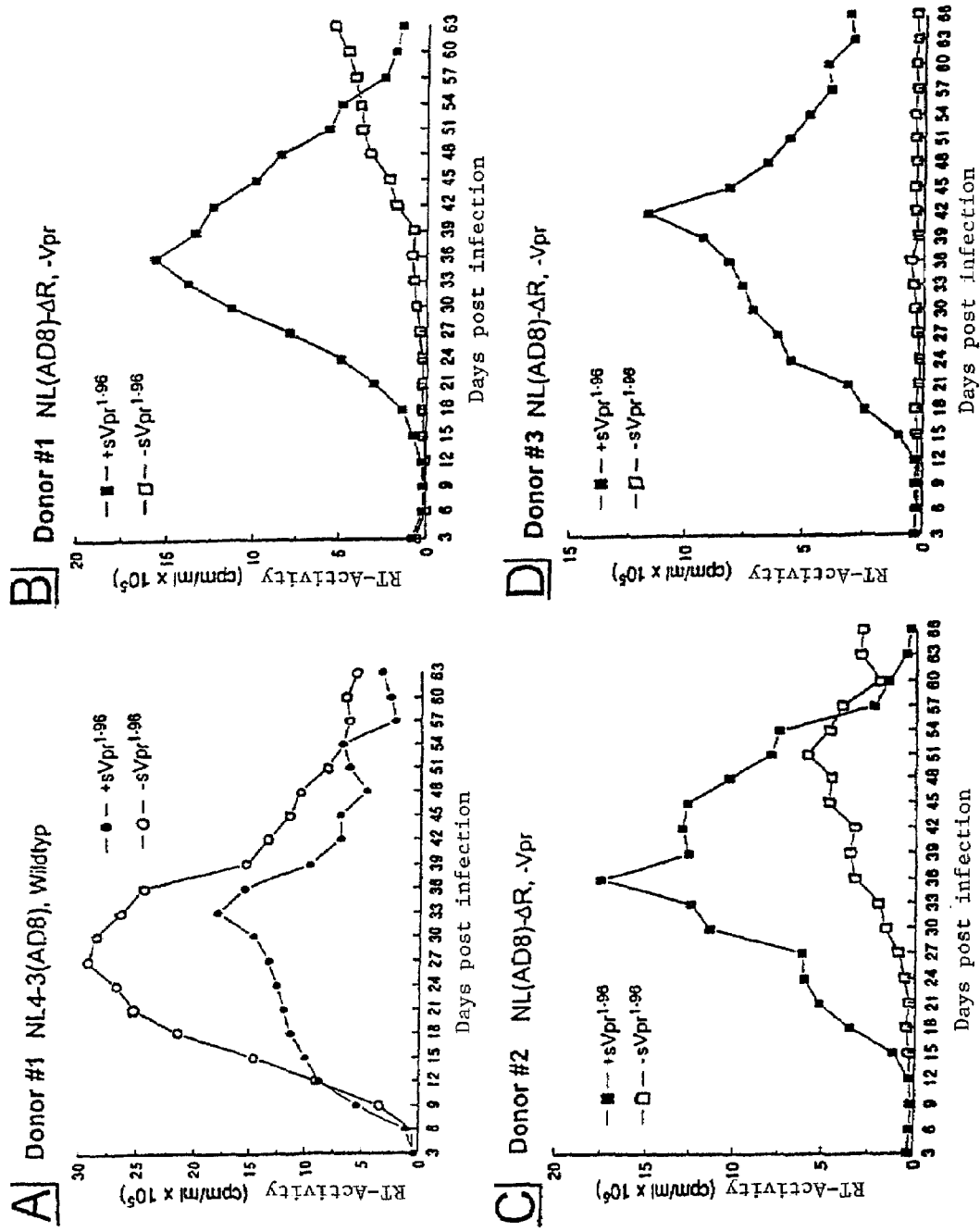

FIG. 4: sVpr$^{1-96}$ activates virus replication of vpr deficient HIV-1 mutant viruses in cultures of primary human monocytes/macrophages isolated from different donors. Parallel cultures of differentiated MDM isolated from three different donors were infected with equal infectious doses of purified virus stocks of the macrophage-tropic virus NL4-3(AD8) as well as the vpr-deficient mutant NL(AD8)deltaR. Virus production was followed over a time frame of two months and release of virus associated RT-activity was plotted against time.

FIG. 5: 2D $^1$H TOCSY spectrum.

Mixing time was 110 ms, the spectrum was recorded of a 2 mM solution of sVpr$^{1-96}$ in 1:1 (v/v) TFE-d2/H2 at 300°K. The x- and y-axes demonstrating the respective 1D $^1$H spectra. Enlargements of regions A, B and C are shown in FIG. 6.

Figure 6:
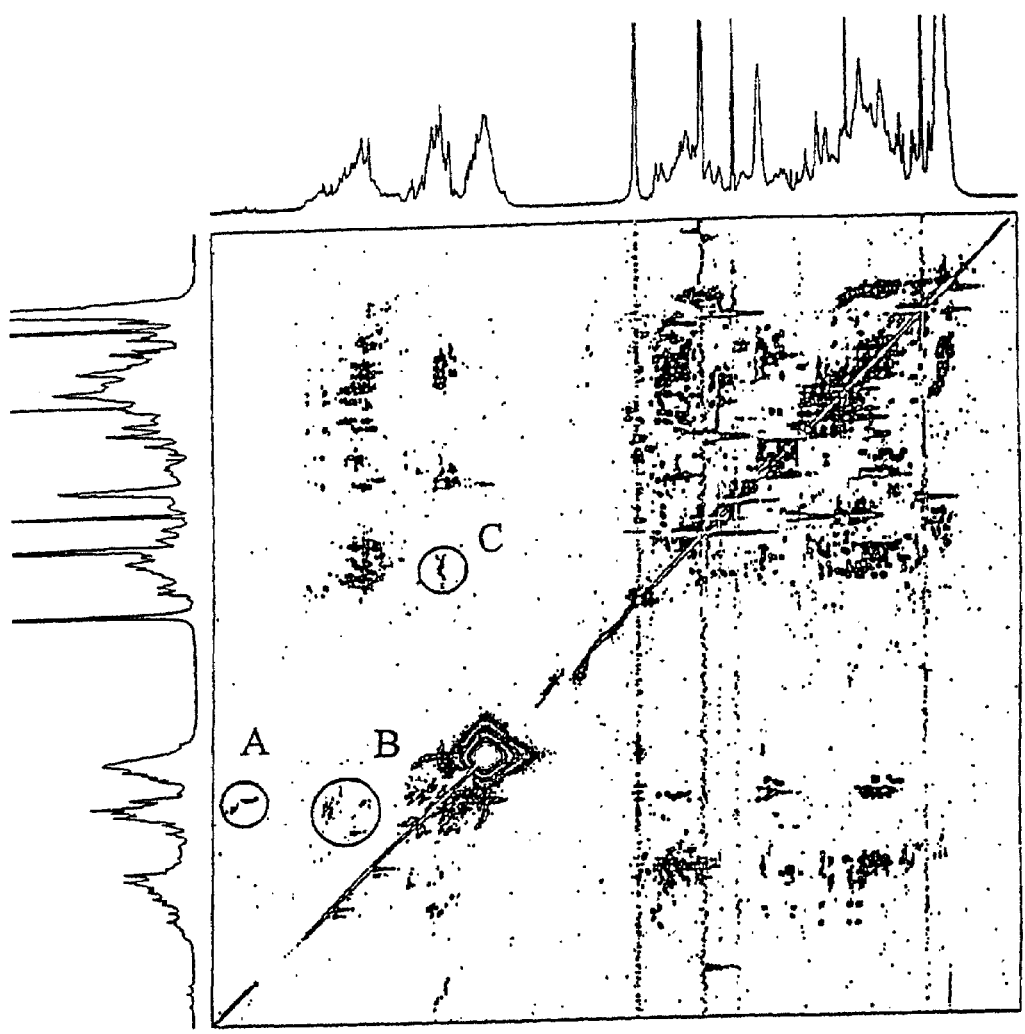

FIG. 6: Enlargements of regions of a 2D TOCSY spectrum shown in FIG. 5 that correlates to interaction of protons between proline H-7 and H-2 of tryptophan residues (A); H-2 and H-4 of histidine residues (B), and epsilon-H and alpha-H of arginine residues (C).

FIG. 7: sVpr$^{1-96}$—HPLC chromatogram and mass spectrum.

Figure 8:
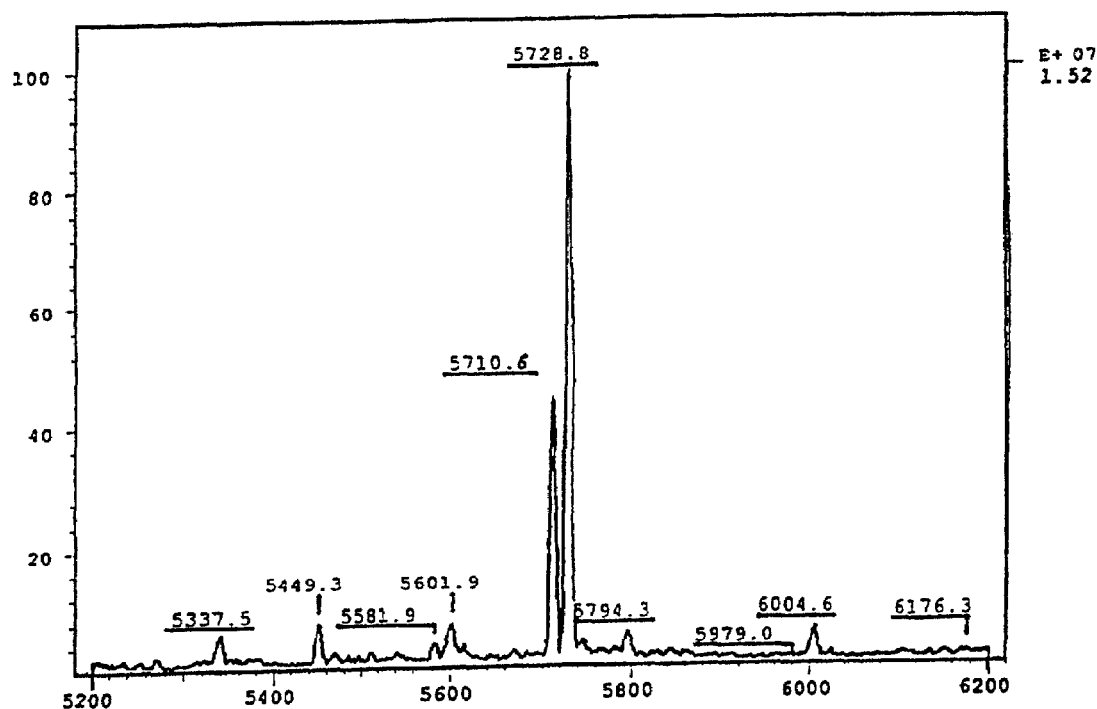

FIG. 8: sVpr$^{1-47}$—mass spectrum.

Figure 9:
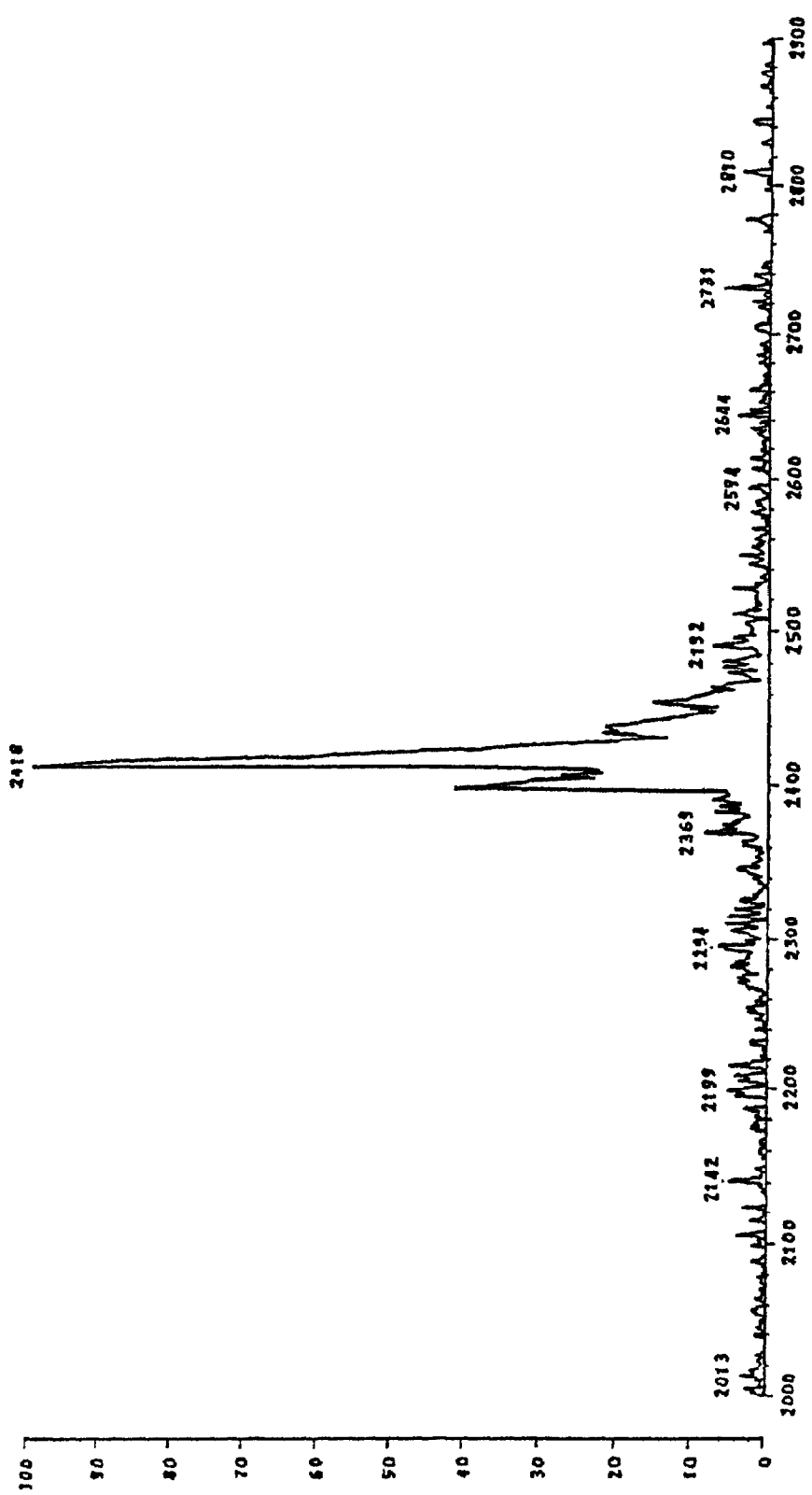

FIG. 9: sVpr$^{1-20}$—mass spectrum.

Figure 10:
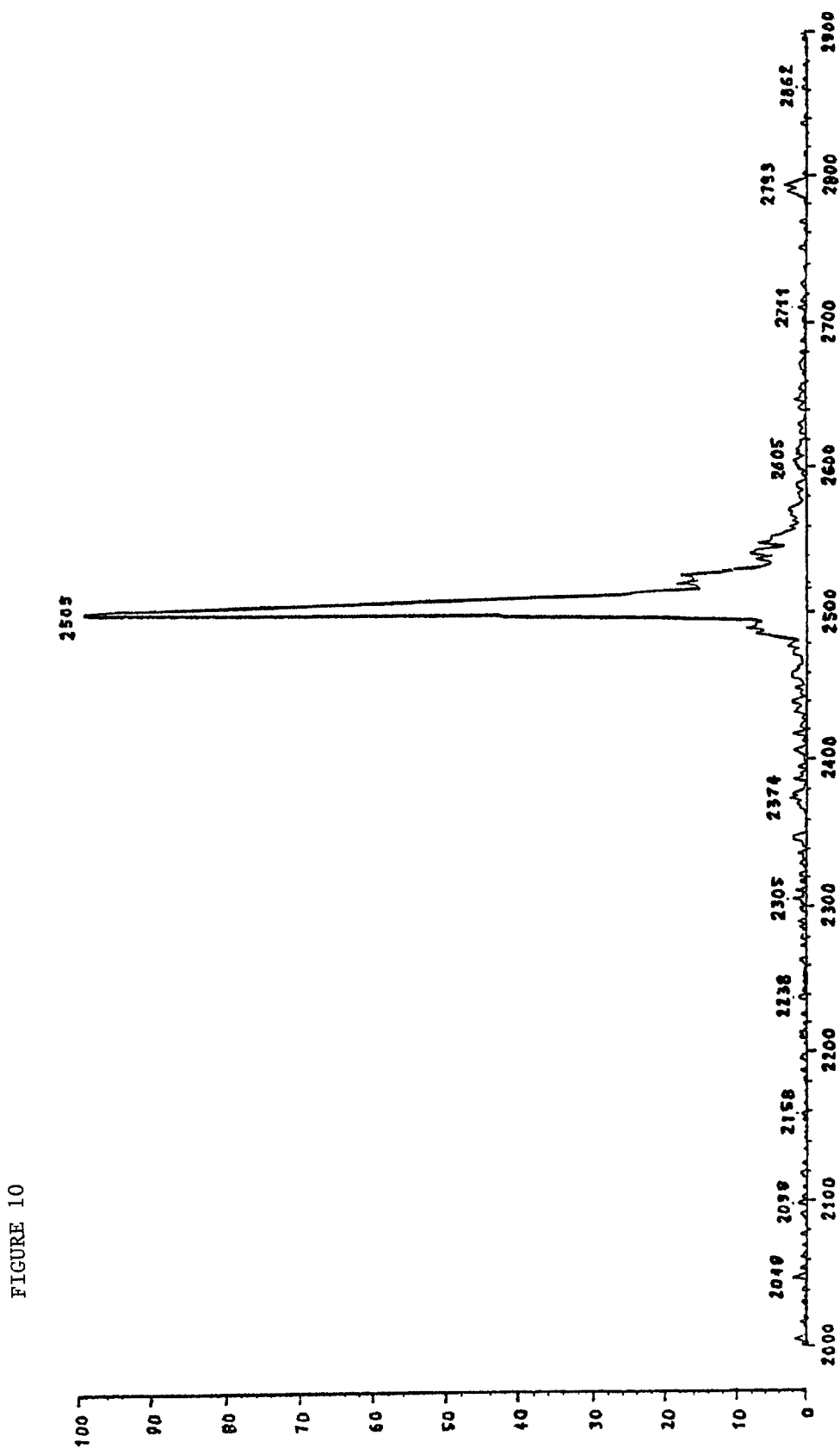

FIG. 10: sVpr$^{21-40}$—mass spectrum.

What is claimed is:

1. A soluble peptide made by solid phase synthesis comprising all or a fragment or variant of a regulatory virus protein R (Vpr) of the human immunodeficiency virus type 1(HIV-1) (SEQ ID NO: 1), wherein the fragment or variant thereof consists of a peptide selected from the group consisting of:
   (a) a 20 amino acid Vpr protein (sVpr$^{1-20}$ or sVpr$^{21-40}$; SEQ ID NO: 8 and 9, respectively);
   (b) a 47 amino acid N-terminal peptide (sVpr$^{1-47}$; SEQ ID NO: 2);
   (c) a 49 amino acid long C-terminal peptide (sVpr$^{48-96}$; SEQ ID NO: 3);
   (d) sVpr$^{11-25}$ (SEQ ID NO: 4); or
   (e) sVpr$^{46-60}$ (SEQ ID NO: 6).

2. The synthetic peptide of claim 1, consisting of sVpr$^{1-96}$ (SEQ ID NO: 1).

3. The synthetic peptide of claim 1 bound to a second molecule, wherein the second molecule comprises a DNA or protein molecule.

4. The synthetic peptide of claim 2 bound to a second molecule, wherein the second molecule comprises a DNA or protein molecule.

5. A composition comprising the synthetic peptide of claim 1 and a carrier.

6. A composition comprising the synthetic peptide of claim 2 and a carrier.

7. A composition comprising the synthetic peptide of claim 3 and a carrier.

8. A composition comprising the synthetic peptide of claim 4 and a carrier.

9. A biological assay product comprising a synthetic peptide of claim 1 immobilized on a substrate.

10. A biological assay product comprising a peptide of claim 2 immobilized on a substrate.

11. The biological assay product of claim 9, wherein the substrate comprises an ELISA carrier surface.

12. The biological assay produce of claim 10, wherein the substrate comprises an ELISA carries surface.

* * * * *

UNITED STATES PATENT AND TRADEMARK OFFICE
CERTIFICATE OF CORRECTION

PATENT NO. : 6,984,486 B1  Page 1 of 1
APPLICATION NO. : 09/913927
DATED : January 10, 2006
INVENTOR(S) : Ulrich Schubert et al.

It is certified that error appears in the above-identified patent and that said Letters Patent is hereby corrected as shown below:

Column 18, line 45, claim 12, "carries" should read --carrier--.

Signed and Sealed this

Twelfth Day of September, 2006

JON W. DUDAS
*Director of the United States Patent and Trademark Office*

SEQUENCE LISTING

<160> NUMBER OF SEQ ID NOS: 11

<210> SEQ ID NO 1
<211> LENGTH: 96
<212> TYPE: PRT
<213> ORGANISM: Artificial Sequence

```
<220> FEATURE:
<223> OTHER INFORMATION: Synthetic peptide of regulatory virus proteins
      R (vpr) of human immunodeficiency virus type 1 (HIV-1)

<400> SEQUENCE: 1

Met Glu Gln Ala Pro Glu Asp Gln Gly Pro Gln Arg Glu Pro Tyr Asn
 1               5                  10                  15

Glu Trp Thr Leu Glu Leu Leu Glu Glu Leu Lys Ser Glu Ala Val Arg
            20                  25                  30

His Phe Pro Arg Ile Trp Leu His Asn Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Arg Gln Arg Ala Arg Asn Gly Ala Ser Arg Ser
                85                  90                  95

<210> SEQ ID NO 2
<211> LENGTH: 47
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 2

Met Glu Gln Ala Pro Glu Asp Gln Gly Pro Gln Arg Glu Pro Tyr Asn
 1               5                  10                  15

Glu Trp Thr Leu Glu Leu Leu Glu Glu Leu Lys Ser Glu Ala Val Arg
            20                  25                  30

His Phe Pro Arg Ile Trp Leu His Asn Leu Gly Gln His Ile Tyr
        35                  40                  45

<210> SEQ ID NO 3
<211> LENGTH: 49
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 3

Glu Thr Tyr Gly Asp Thr Trp Ala Gly Val Glu Ala Ile Ile Arg Ile
 1               5                  10                  15

Leu Gln Gln Leu Leu Phe Ile His Phe Arg Ile Gly Cys Arg His Ser
            20                  25                  30

Arg Ile Gly Val Thr Arg Gln Arg Ala Arg Asn Gly Ala Ser Arg
        35                  40                  45

Ser

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 4

Gln Arg Glu Pro Tyr Asn Glu Trp Thr Leu Glu Leu Leu Glu Glu
 1               5                  10                  15
```

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 5

Asn Leu Gly Gln His Ile Tyr Glu Thr Tyr Gly Asp Thr Trp Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 6

Ile Tyr Glu Thr Tyr Gly Asp Thr Trp Ala Gly Val Glu Ala Ile
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 7

Gly Val Glu Ala Ile Ile Arg Ile Leu Gln Gln Leu Leu Phe Ile
 1               5                  10                  15

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 8

Met Glu Gln Ala Asn Glu Asp Gln Gly Asn Gln Arg Glu Asn Tyr Asn
 1               5                  10                  15

Glu Trp Thr Leu
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 9

Glu Leu Leu Glu Glu Leu Lys Ser Glu Ala Val Arg His Phe Asn Arg
 1               5                  10                  15

Ile Trp Leu His
            20

<210> SEQ ID NO 10

```
-continued

<211> LENGTH: 15
<212> TYPE: PRT
<213> ORGANISM: Artificial Sequence
<220> FEATURE:
<223> OTHER INFORMATION: sVpr66-80

<400> SEQUENCE: 10

Gln Leu Leu Phe Ile His Phe Arg Ile Gly Cys Arg His Ser Arg
 1               5                  10                  15

<210> SEQ ID NO 11
<211> LENGTH: 21
<212> TYPE: PRT
<213> ORGANISM: Artificial Sequence
<220> FEATURE:
<223> OTHER INFORMATION: sVpr76-96

<400> SEQUENCE: 11

Cys Arg His Ser Arg Ile Gly Val Thr Arg Gln Arg Arg Ala Arg Asn
 1               5                  10                  15

Gly Ala Ser Arg Ser
            20
```